United States Patent [19]

Grover et al.

[11] Patent Number: 4,962,095
[45] Date of Patent: Oct. 9, 1990

[54] METHOD OF REDUCING PRE-AND POST-ISCHEMIC MYOCARDIAL ARRHYTHMIAS AND FIBRILLATION

[75] Inventors: Gary J. Grover, Stockton, N.J.; James L. Bergey, Lansdale, Pa.

[73] Assignee: E. R. Squibb & Sons, Inc., Princeton, N.J.

[21] Appl. No.: 451,667

[22] Filed: Dec. 18, 1989

Related U.S. Application Data

[62] Division of Ser. No. 311,321, Feb. 15, 1989.

[51] Int. Cl.$^5$ .......................................... A61K 31/675
[52] U.S. Cl. ...................................................... 514/91
[58] Field of Search ........................................ 514/91

[56] References Cited

U.S. PATENT DOCUMENTS 4,745,196  5/1988  Karanewsky et al. ............... 548/413
4,808,413  1/1989  Joshi et al. ........................... 424/458

OTHER PUBLICATIONS

Rochette et al., "Protective Effect of ACE Inhibitors . . . "Clin. and Exper.-Theory and Practice, A9 (2&3), 365–368 (1987).

Westlin et al., "Does Captopril Attenuate Reperfusion-Induced Myocardial Dysfunction by Scavenging Free Radicals?", Circulation, vol. 77 (Suppl I), pp. 30–39, Jun. 1988.

van Gilst et al., "Reduction of Reperfusion Arrhythmias in the Ischemic Isolated Rat Heart by ACE Inhibitors . . . ", J. Cardiovacs Pharmacol, vol. 8, No. 4, 722–728, 1986.

Li et al., "Protective Effects of Captopril and Enalopril on Myocardial Ischemia and Reperfusion Damage of Rat", J. Mol. Cardiol, vol. 19, pp. 909–915 (1987).

van Gilst et al., "Captopril Reduces Purine Loss and Reperfusion Arrhythmi in the Rat Heart after Coronary Artery Occulsion, " European Jour. of Pharmacology, vol. 100, pp. 113–117 (1984).

De Graeff et al., "Concentration-Dependent Protection by Captopril Against Ischemia-Reperfusion Injury in the Isolated Rat Heart", Arch., int. Pharmacodyn., vol. 280, pp. 181–193 (1986).

De Graeff et al. "Concentration-Dependent Protection by Captopril Against Myocardial Damage During Ischemia and Reperfusion in a Closed Chest Pig Model", Jour of Cardiovascular Pharmacology, 9 (Suppl. 2) pp. S37–42 (1987).

Primary Examiner—Robert Gerstl
Attorney, Agent, or Firm—Stephen B. Davis

[57] ABSTRACT

Zofenopril, fosinopril, (S)-1-[6-amino-2-[[hydroxy (4-phenylbutyl) phosphinyl]oxy]-1-oxohexyl]-L-proline or a pharmaceutically acceptable salt thereof alone or in combination with a thrombolytic, antiarrhythmic, or antifibrillatory agent is employed to reduce pre-and post- ischemic myocardial arrhythmias and fibrillations as well as reducing arrhythmias associated with congestive heart failure.

5 Claims, No Drawings

METHOD OF REDUCING PRE-AND POST-ISCHEMIC MYOCARDIAL ARRHYTHMIAS AND FIBRILLATION

This is a division of application Ser. No. 311,321, filed on Feb. 15, 1989.

FIELD OF THE INVENTION

The present invention relates to a method of reducing pre- and post-ischemic myocardial arrhythmias and fibrillation as well as reducing arrhythmias associated with congestive heart failure in mammalian species by administering zofenopril, fosinopril, (S)-1-[6-amino-2-[[hydroxy-(4-phenylbutyl)phosphinyl]oxy]-1-oxohexyl]-L-proline, or a pharmaceutically acceptable salt thereof alone or in combination with a thrombolytic agent or other antiarrhythmic or antifibrillatory agents.

BACKGROUND OF THE INVENTION

Blood flow reductions in the heart can result in dysfunction of this organ and cell death if the flow reduction is severe enough. Restoration of coronary blood flow early during a heart attack is becoming a clinical reality with the advent and improvements in thrombolytic, mechanical, and surgical interventions. While early restoration of blood flow, for example, by thrombolysis or following transient ischemia, can prevent or mitigate the degree of cell death (infarction) occurring, reperfusion can still result in marked cardiac arrythmia or fibrillation. These arrythmias can often lead to sudden death. Thus, it would be of great clinical value to find a means to preserve the reperfusion function of the heart.

Zofenopril which chemically is named [1(R*),2α,4α]-1-[3-(benzoylthio)-2-methyl-1-oxopropyl]-4-(phenylthio)-L-proline has been reported as being an antihypertensive agent due to its angiotensin converting enzyme inhibition activity. Zofenopril, its pharmaceutically acceptable salts, and its method of preparation are described by Ondetti et al. in U.S. Pat. No. 4,316,906.

Fosinopril which chemically is named (trans)-4-cyclohexyl-1-[[[2-methyl-1-(1-oxopropoxy)propoxy](4-phenylbutyl)phosphinyl]acetyl]-L-proline has been reported as being an antihypertensive agent due to its angiotensin converting enzyme inhibition activity. Fosinopril, its pharmaceutically acceptable salts, and its method of preparation are described by Petrillo in U.S. Pat. Nos. 4,337,201 and 4,384,123.

(S)-1-[6-Amino-2-[[hydroxy(4-phenylbutyl)phosphinyl]oxy]-1-oxohexyl]-L-proline, pharmaceutically acceptable salts thereof, its method of preparation, and its activity as an antihypertensive agent due to its angiotensin converting enzyme inhibition activity are described by Karanewsky et al. in U.S. Pat. No. 4,745,196.

DESCRIPTION OF THE INVENTION

The present invention is directed to a method for treating pre- and post-ischemic arrhythmias and fibrillation as well as treating arrhythmias associated with congestive heart failure in mammalian species thus improving heart function. Accordingly, a therapeutically effective amount of zofenopril, fosinopril, (S)-1-[6-amino-2-[[hydroxy(4-phenylbutyl)phosphinyl]oxy]-1-oxohexyl]-L-proline, or a pharmaceutically acceptable salt thereof is systemically administered alone or in combination with other therapeutic agents during or soon after reperfusion, i.e., within four to six hours of a myocardial infarction. Methods of systemic administration include oral, parenteral, and by catheter. In addition, the above described drug therapy may be combined with other methods of reperfusion such as percutaneous translumenal angioplasty (PTCA), cardiopulmonary bypass and graft (CABG) procedures.

The term "reperfusion" is employed herein to refer to release or reversal of occlusion and resumption of blood flow.

Among the classes of other therapeutic agents useful within the method of this invention are thrombolytic agents, antiarrhythmic, and antifibrillatory agents. Suitable thrombolytic agents include tissue plasminogen activator (tPA), recombinant tPA, streptokinase, urokinase, prourokinase, and anisoylated plasminogen streptokinase activator complex (APSAC, Eminase, Beecham Laboratories). Suitable antiarrhythmic and antifibrillatory agents include quinidine, procainamide, disopyramide, lidocaine, tocainide, phenyltoin, flecaimide, encainide, amiodarone and other class I agents; class III agents such as bretylium and clofilium; class IV agents such as verapamil and diltiazem; and β-adrenergic receptor blocking agents such as propanolol, sotalol, nadolol, metoprolol or other class II agents which affect nervous input to the heart. The classification method for the above antiarrhythmic agents was the Vaughan Williams classification.

In carrying out the method of the present invention, zofenopril, fosinopril, or (S)-1-[6-amino-2-[[hydroxy(4-phenylbutyl)phosphinyl]oxy]-1-oxohexyl]-L-proline alone or in combination with the above described thrombolytic agents, antiarrhythmic agents, or antifibrillatory agents may be administered to a mammalian species, such as monkeys, dogs, cats, rats, humans, etc. during the period of coronary occlusion and/or during the period of reperfusion and/or shortly after termination of the ischemic attack, for example within 1 to 2 hours after the ischemia, within 24 to 48 hours after the ischemia and for weeks and months thereafter.

The single drug therapy or combination drug therapy described above may be administered systemically, such as orally or parenterally, within one hour after the ischemia. It is preferred that the drug therapy selected be administered locally, as soon after the ischemic attack as possible, to the coronary arteries by catheter such as by arterial angiography or intracoronary injection.

The dose of zofenopril, fosinopril, (S)-1-[6-amino-2-[[hydroxy(4-phenylbutyl)phosphinyl]oxy]-1-oxohexyl]-L-proline, or pharmaceutically acceptable salt thereof whether alone or in combination with the other active agents will be employed in an amount of from about 0.005 to about 30 mg/kg/treatment, preferably from about 0.01 to about 3 mg/kg/treatment, when administered during arterial angiography by intracoronary injection or intravenously. The number of treatments will depend upon the length of the ischemic attack and the progress of reperfusion to achieve normal heart function. Usually, from 1 to 5 treatments per day will be required for as long as contractile dysfunction continues.

The other therapeutic agents will be employed in amounts as indicated in the Physician's Desk Reference (PDR), 42nd Edition, 1988. Thus, Hoechst's Streptasse® brand of streptokinase may be administered as follows:

TABLE I

Suggested Dilutions and Infusion Rates

| Streptase ® (streptokinase) Dosage/Infusion Rate | Streptase ® (streptokinase) Vial Content Needed | Total Volume of Solution (mL) | Infusion Pump Rate |
|---|---|---|---|
| I. Intracoronary Artery Administration | | | |
| A. Bolus Injection 20,000 IU | 1 vial, 250,000 IU* | 125 | Inject 10 mL |
| B. Maintenance Dose 2,000 IU/min | | | 60 mL per hour |
| II. Intravenous Administration | | | |
| A. Loading Dose 250,000 IU/30 min | (a) 1 vial, 250,000 IU or | 45 | 90 mL per hour for 30 min |
| | (b) 1 vial, 750,000 IU | 45 | 30 mL per hour for 30 min |
| B. Maintenance Dose 100,000 IU/hr | 1 vial, 750,000 IU | 45** | 6 mL per hour |

*sufficient for Bolus Injection and Maintenance Dose
**If necessary, total volume may be increased, in increments of 45 mL, to a maximum of 500 mL with the infusion pump rate increased accordingly. The total volume of 45 mL or multiple thereof is recommended.

tPA employed herein may be Genentech's Activase ®, Alteplase which, as described in the Physician's Desk Reference (PDR), 42 Ed., 1988, Supplement A, pp. A71 and A72 is as follows.

Activase ®, Alteplase, a sterile, white to off-white, lyophilized powder, is intended for intravenous administration after reconstitution with sterile water for injection, U.S. Patent. The quantitative composition of the lyophilized product is:

| 50 mg. (29 million IU) Vial | 20 mg. (11.6 million IU) Vial |
|---|---|
| Alteplase 50 mg. (29 million IU) | Alteplase 20 mg. (11.6 million IU) |
| L-Arginine 1.7 g. | L-Arginine 0.7 g. |
| Phosphoric Acid 0.5 g. | Phosphoric Acid 0.2 g. |
| Polysorbate 80, less than 4 mg. | Polysorbate 80, less than 1.6 mg. |

Phosphoric acid and/or sodium hydroxide may be used prior to lyophilization for pH adjustment.

Biological potency is determined by an in vitro clot lysis assay and is expressed in International Units as tested against the WHO standard. The specific activity of Activase ®, Alteplase, is 580,000 IU/mg.

The recommended dose is 100 mg. administered as 60 mg. (34.8 million IU) in the first hour (of which 6 to 10 mg. is administered as a bolus over the first 1-2 minutes), 20 mg. (11.6 million IU) over the second hour, and 20 mg. (11.6 million IU) over the third hour. For smaller patients (less than 65 kg.), a dose of 1.25 mg/kg administered over 3 hours, as described above, may be used.

Abbott's Abbokinase brand of urokinase may be administered after heparin dosing of 2,500 to 10,000 units IV, in an amount by infusion into the occluded artery at a rate of 4 ml. per minute (6,000 IU per minute) for periods of up to 2 hours.

Prourokinase may be administered in conventional dosages normally used in clinical practice such as a 7.5 bolus followed by 40.5 mg. IV for 1 hour or 66.5 mg. IV for 1 hour.

APSAC (Eminase) may be administered in conventional dosages normally used in clinical practice such as a single 30 unit IV dosage.

Where the zofenopril, fosinopril, (S)-1-[6-amino-2-[[hydroxy(4-phenylbutyl)phosphinyl]oxy]-1-oxohexyl]-L-proline, or pharmaceutically acceptable salt thereof or the combination of one of these agents with a thrombolytic, antiarrhythmic, or antifibrillitory agent is to be administered by angiography, intravenously, or intacoronary injection, it will be formulated in conventional vehicles, such as distilled water, saline, Ringer's solution or other conventional carriers.

The above described agents or combination of agents may also be incorporated in a conventional dosage form, such as a tablet, capsule, elixir or injectable. The above dosage forms will also include the necessary carrier material, excipient, lubricant, buffer, antibacterial, bulking agent (such as mannitol), antioxidants (ascorbic acid of sodium bisulfite) or the like. Oral dosage forms are preferred although parenteral forms are also satisfactory.

With regard to such systemic formulations, single or divided doses of from about 5 to about 2500 mg., preferably from about 10 to 2000 mg/one to four times daily, may be administered in systemic dosage forms as described above for a period sufficient to restore normal heart function.

The dose administered must be carefully adjusted according to age, weight and condition of the patient, as well as the route of administration, dosage form and regimen and the desired result.

Thus, for oral administration, a satisfactory result may be obtained employing zofenopril, fosinopril, (S)-1-[6-amino-2-[[hydroxy(4-phenylbutyl)phosphinyl]oxy]-1-oxohexyl]-L-proline, or a pharmaceutically acceptable salt thereof in an amount within the range of from about 0.01 mg/kg to about 100 mg/kg and preferably from about 0.1 mg/kg to about 25 mg/kg alone or in combination with the thrombolytic agent, antiarrhythmic agent, or antifibrillatory agent in an amount within the range of from about 0.1 mg/kg to about 100 mg/kg and preferably from about 0.1 mg/kg to about 25 mg/kg with the agents being employed together in the same oral dosage form or in separate oral dosage forms taken at the same time.

A preferred oral dosage form, such as tablets or capsules, will contain zofenopril, fosinopril, or (S)-1-[6-amino-2-[[hydroxy(4-phenylbutyl)phosphinyl]oxy]-1-oxohexyl]-L-proline in an amount of from about 0.1 to about 500 mg. preferably from about 125 to about 200 mg., and more preferably from about 25 to about 150 mg., alone or with the thrombolytic agent, antiarrhythmic agent or antifibrillatory agent in an amount of from about 1 to about 350 mg., preferably from about 2 to 200 mg., and more preferably from about 30 to about 150 mg.

For parenteral administration, zofenopril, fosinopril, (S)-1-[6-amino-2-[[hydroxy(4-phenylbutyl)phosphinyl]oxy]-1-oxohexyl]-L-proline, or a pharmaceutically acceptable salt thereof will be employed in an amount within the range of from about 0.005 mg/kg to about 10 mg/kg and preferably from about 0.01 mg/kg to about 1 mg/kg, alone or with the thrombolytic agent, antiarrhythmic agent, or antifibrillatory agent in an amount within the range of from about 0.005 mg/kg to about 20 mg/kg and preferably from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg. in total weight containing one or more of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in conventional liquid vehicle acceptable for pharmaceutical administration so as to provide the desired dosage in one to four teaspoonful.

Such dosage forms can be administered to the patient on a regimen of one to four doses per day.

EXAMPLE 1

An injectable solution for use in carrying out the method of this invention by arterial angiography or intravenous administration was prepared as follows:

| | |
|---|---|
| Zofenopril calcium | 500 mg. |
| Methyl paraben | 5 mg. |
| Propyl paraben | 1 mg. |
| Sodium chloride | 25 g. |
| Water for injection qs. | 5 l |

The zofenopril calcium, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

Similar injectable solutions can be prepared by employing fosinopril sodium or (S)-1-[6-amino-2-[[hydroxy(4-phenylbutyl)phosphinyl]oxy]-1-oxohexyl]-L-proline, dilithium salt in place of the zofenopril calcium.

EXAMPLE 2

Tablets for use in reducing pre- and post-ischemic arrhythmias were prepared as set forth below.

1000 tablets each containing 100 mg. of active ingredient were produced from the following ingredients:

| | |
|---|---|
| Zofenopril | 100 g. |
| Cornstarch | 50 g. |
| Gelatin | 7.5 g. |
| Avicel (microcrystalline cellulose) | 25 g. |
| Magnesium stearate | 2.5 g. |

The zofenopril calcium and cornstarch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg. of active ingredient which is used for carrying out the method of this invention.

Similar tablets can be prepared by employing fosinopril sodium or (S)-1-[6-amino-2-[[hydroxy(4-phenylbutyl)phosphinyl]oxy]-1-oxohexyl]-L-proline, dilithium salt in place of the zofenopril calcium.

EXAMPLE 3

The injectable solution of Example 1 may be employed in conjunction with conventional dosage forms of the thrombolytic agent, antiarrhythmic agent, or antifibrillating agent for treating pre- and post- ischemic myocardial arrhythmias and fibrillation as well as treating arrhythmias associated with congestive heart failure.

What is claimed is:

1. A method of reducing pre- and post-ischemic arrhythmias and fibrillation as well as reducing arrhythmias associated with congestive heart failure in a mammalian species which comprises administering to a mammalian species in need of such treatment an effective amount of (S)-1-[6-amino-2-[[hydroxy(4-phenylbutyl)phosphinyl]oxy]-1-oxohexyl]-L-proline or a pharmaceutically acceptable salt thereof alone or in combination with a thrombolytic agent, antiarrhythmic agent, or antifibrillatory agent or with a non-pharmaceutical reperfusion technique.

2. The method of claim 1 wherein the only therapeutic agent employed is (S)-1-[6-amino-2-[[hydroxy(4-phenylbutyl)phosphinyl]oxy]-1-oxohexyl]-L-proline or a pharmaceutically acceptable salt thereof.

3. The method of claim 1 wherein the agents employed are (S)-1-[6-amino-2-[[hydroxy(4-phenylbutyl)phosphinyl]oxy]-1-oxohexyl]-L-proline or a pharmaceutically acceptable salt thereof and a thrombolytic agent, an antiarrhythmia agent, or an antifibrillatory agent.

4. The method of claim 3 wherein the other agent is a thrombolytic agent selected from the group consisting of tissue plasminogen activator (tPA), recombinant tissue plasminogen activator, streptokinase, urokinase, and prourokinase.

5. The method of claim 3 wherein the other agent is an antiarrhythmic or antifibrillatory agent selected from the group consisting of quinidine, procainamide, disopyramide, lidocaine, tocainide, phenyltoin, flecainide, encainide, amiodarone, bretylium, clofilium, verapamil, diltiazem, propanolol, sotalol, nadolol, and metoprolol.

* * * * *